United States Patent
Moe et al.

(10) Patent No.: US 6,174,331 B1
(45) Date of Patent: Jan. 16, 2001

(54) HEART VALVE LEAFLET WITH REINFORCED FREE MARGIN

(75) Inventors: Riyad E. Moe, Austin; Xiao Yan Gong, Round Rock; Edward Sarnowski, Austin, all of TX (US)

(73) Assignee: Sulzer Carbomedics Inc., Austin, TX (US)

(*) Notice: Under 35 U.S.C. 154(b), the term of this patent shall be extended for 0 days.

(21) Appl. No.: 09/356,936

(22) Filed: Jul. 19, 1999

(51) Int. Cl.$^7$ ........................................... A61F 2/24
(52) U.S. Cl. ............................... 623/2.12; 623/901
(58) Field of Search ..................... 623/2.12–2.19, 623/901

(56) References Cited

U.S. PATENT DOCUMENTS

| | | | |
|---|---|---|---|
| 4,265,694 | 5/1981 | Boretos et al. | 156/242 |
| 4,364,127 | * 12/1982 | Pierce et al. | 623/2.15 |
| 4,473,423 | 9/1984 | Kolff | 156/245 |
| 4,778,461 | 10/1988 | Pietsch et al. | 623/2 |
| 4,888,009 | 12/1989 | Lederman et al. | 623/2 |
| 5,116,564 | 5/1992 | Jansen et al. | 264/255 |
| 5,500,016 | * 3/1996 | Fisher | 623/2.12 |
| 5,562,729 | 10/1996 | Purdy et al. | 623/2 |
| 5,713,953 | * 2/1998 | Vallana et al. | 623/2.12 |
| 6,117,169 | * 9/2000 | Moe | 623/2.12 |

FOREIGN PATENT DOCUMENTS

WO 98/32400   7/1998   (WO).

OTHER PUBLICATIONS

Hamid, M.S., et al., Influence of Stent Height Upon Stresses on the Cusps of Closed Bioprostheticvalves, J. Biomechanics vol. 19, No. 9 pp. 759–769, 1986.

Fisher, J., et al., An Improved Pericardialbioprostheticheart Valve, European Journal of Cardiothoracic Surgery (1987) 1:71–79.

Christie, G.W., et al., On Stress Reduction in Bioprostheticheart Valve Leaflets by the Use of a Flexible Stent, Journal of Cardiac Surgery, vol. 6, No. 4, 1991, pp. 476–481.

Christie, G.W., The Bovine Pericardialbioprostheticheart Valve: Methods for Tensile Stress Reduction in the Leaflets During the Loaded Phase, Bed–vol. 20, 1991, pp. 647–650.

* cited by examiner

Primary Examiner—David H. Willse
Assistant Examiner—Suzette J. Jackson
(74) Attorney, Agent, or Firm—Timothy L. Scott

(57) ABSTRACT

A flexible leaflet heart valve includes a base, a peripheral portion and a plurality of leaflets. Each leaflet includes a scalloped free margin having opposite ends and a mid-portion between the opposite ends. The opposite ends are attached to the peripheral portion of the valve at a first height above the base. The mid-portion of each free margin is positioned at a second height above the base, less than the first height. Each free margin is adjacent each other free margin to form a gap therebetween. Each leaflet is of a first thickness and at least a portion of each free margin is of a second thickness, greater than the first thickness. This may include extending the second thickness along the entire free margin between the opposite ends or extending the second thickness only along the mid-portion of the free margin.

23 Claims, 5 Drawing Sheets

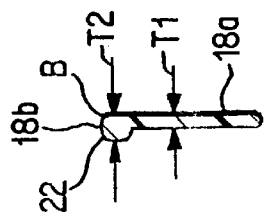
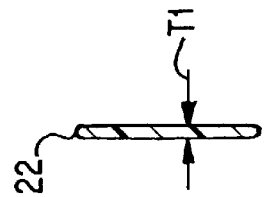
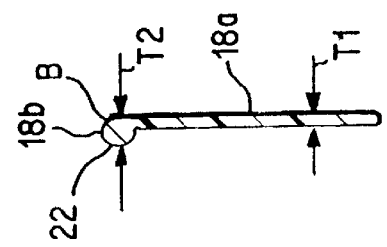
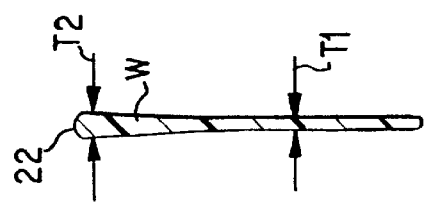
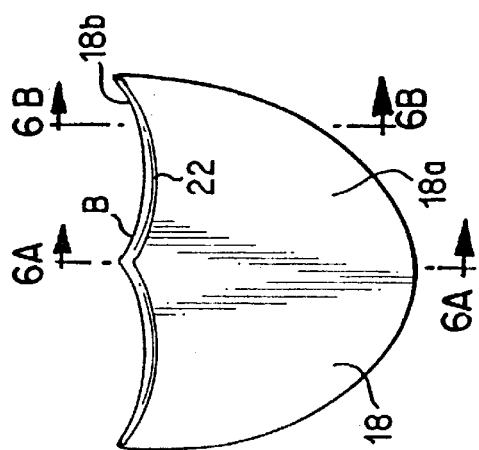
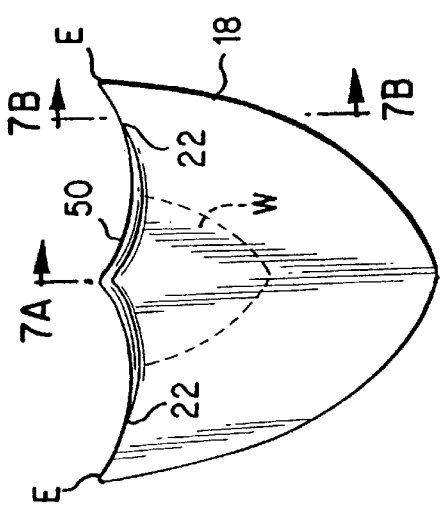

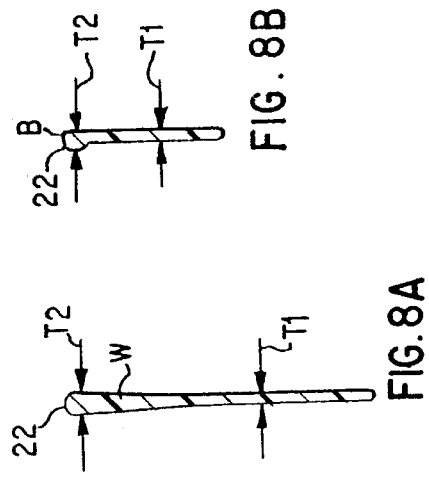
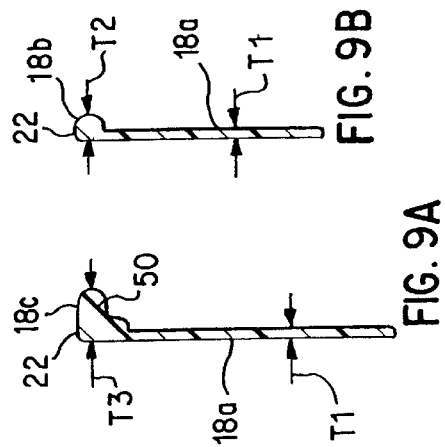
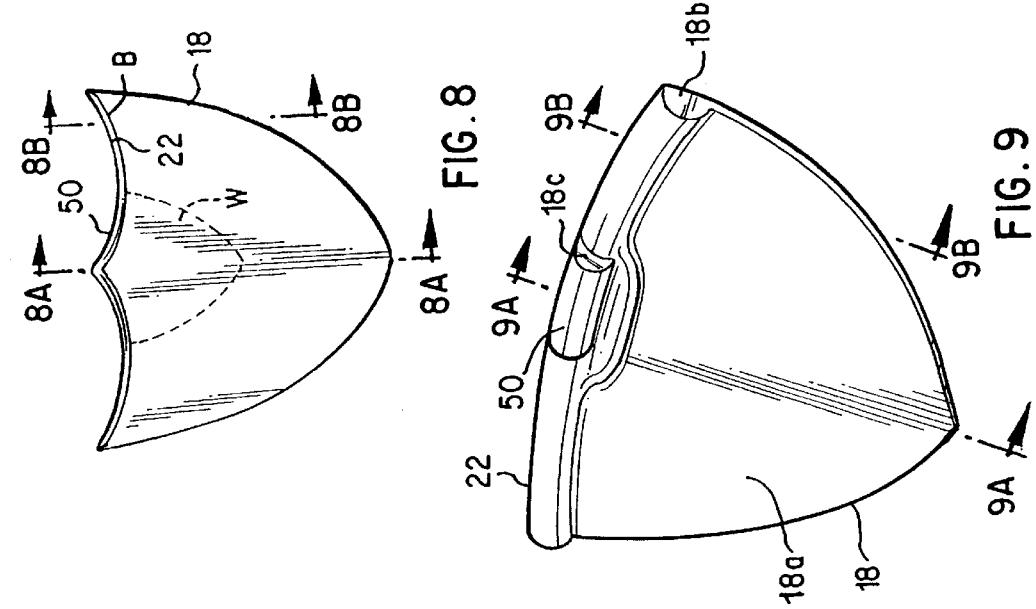

HEART VALVE LEAFLET WITH REINFORCED FREE MARGIN

BACKGROUND

The disclosures herein relate generally to heart valves and more particularly to tri-leaflet polymer valves.

Heart valves include mechanical valves, tissue valves and polymer valves. A heart valve is implanted into an annular opening in a heart created when a diseased valve is removed. The valve can be secured in the annulus of the opening through the use of sutures or pins that penetrate the host tissue and an outside edge of the valve. Alternatively the valve can then be secured in the annulus by suturing the host tissue to the sewing ring. Heart valves function essentially as a one-way check valve.

Early heart valve prostheses included ball-and-cage valves and disc-and-cage valves in which a ball or a disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or "regurgitate", the energy of the blood flow forced the ball or disc into the orifice in the valve and blocked the flow of blood.

A bi-leaflet valve comprised an annular valve body in which two opposed leaflet occluders were pivotally mounted. The occluders were typically substantially rigid, although some designs incorporated flexible leaflets, and moved between a closed position, in which the two leaflets were mated and blocked blood flow in the reverse direction, and an open position, in which the occluders were pivoted away from each other and did not block blood flow in the forward direction. The energy of blood flow caused the occluders to move between their open and closed positions.

A tri-leaflet valve comprised an annular valve body in which three flexible leaflets were mounted to a portion of the valve body, called a "stent," located at the circumference of the annulus. Some tri-leaflet valves used rigid leaflets. When blood flowed in the forward direction, the energy of the blood flow deflected the three leaflets away from the center of the annulus and allowed blood to flow through. When blood flowed in the reverse direction, the three leaflets engaged each other in a coaptive region, occluded the valve body annulus and prevented the flow of blood. The valve leaflets were made from tissue, such as specially treated porcine or bovine pericardial tissue or from a man-made material such as polyurethane or another biocompatible polymer.

In one specific example, U.S. Pat. No. 4,265,694 discloses an artificial tri-leaflet heart valve wherein the entire free margin includes a thickened lip portion combined with reinforcing lines radiating from the base of the valve for reinforcing the leaflets.

In U.S. Pat. No. 4,364,127, a prosthetic heart valve constructed of hemo-compatible materials that is anatomically and functionally similar to the natural aortic valve is disclosed. The heart valve is a tri-leaflet type which has its formed leaflets heat set in a partially open position to reduce pressure required to open the leaflets in response to blood flowing therethrough.

U.S. Pat. No. 4,473,423 discloses an artificial heart valve having thin, seamless leaflets which converge to the center of a frame from the frame's inner wall. The leaflets each have a convex outflow surface and a concave inflow surface. The leaflets meet along adjacent edges to form cusps. Sinus valsalvae sections of the valve are formed as rounded recesses defined in the valve frame's inner wall as continuous curved profiles of the respective leaflet concave surface. The valve is fabricated by vacuum molding techniques whereby layers of elastomer are vacuum formed to comprise the leaflet and sinus valsalvae portions. The leaflets are all formed from two or more layers of elastomer which are cut to define the leaflet edges or commissures. One elastomer layer extends along the frame recess to provide continuity for each leaflet and its sinus valsalvae. The resulting structure has no rims or seams in the inflow or outflow paths.

In U.S. Pat. No. 4,778,461, a heart valve prosthesis for replacing the aortic valve or the pulmonary valve, comprises a support ring with at least two commissure supports and flexible cusps, is characterized in that the height of the support ring including the commissure supports is less than the total height of the heart valve prosthesis.

In U.S. Pat. No. 4,888,009, a prosthetic heart valve comprises a suture ring supporting a stent which surrounds a conduit bearing a plurality of flexible valve leaflets. The conduit extends beyond the end of the suture ring.

U.S. Pat. No. 5,116,564 discloses a method of producing flexible closing members, especially artificial heart valves. The housing of the closing member is radially expanded, the closing element of the closing member is formed as a substantially plane two-dimensional element, and the plane two-dimensional element is connected to the housing in the expanded condition of the same. This method is preferably realized as a dip method according to which the closing element is shaped and formed to the housing in a single working step. The described flexible closing member is an artificial three-sail heart valve which is characterized by a special shape of the three closing elements.

In U.S. Pat. No. 5,500,016, a flexible leaflet heart valve, to replace natural aortic or pulmonary valves of the heart, includes a frame and flexible leaflets attached to the frame. Each flexible leaflet forms part of a surface of revolution having its axis of revolution substantially orthogonal to the direction of blood flow through the valve.

U.S. Pat. No. 5,562,729 discloses a multi-leaflet heart valve composed of a biocompatible polymer which, simultaneously imitates the structure and dynamics of biological heart valves and avoids promotion of calcification. The valve includes a plurality of flexible leaflets dip cast on a mandrel, which leaflets are then bonded with a bonding agent to the interior surfaces of a plurality of struts on a metal-reinforced prosthetic stent. The leaflets open and close in response to the pumping action of the heart. The leaflets and the polymer components of the prosthetic stent are manufactured of biocompatible polymers exhibiting intrinsic calcification-resistant properties.

An important consideration in prosthetic heart valve design is the durability of the heart valve. Replacing a prosthetic heart valve after it has been implanted is inconvenient and expensive for the patient. Mechanical valves may enhance the possibility of clotting. Therefore, patients using mechanical valves are typically required to take anticoagulation medication. Also, mechanical valves are noisy which is most disconcerting to patients. Patients having tissue valve implants are usually not required to take anticoagulation medication. Tissue valves are not noisy like mechanical valves however, they are also not very durable.

Polymer valves are typically molded to a desired shape and then cut to form the free margins of the leaflets. One source of prosthetic heart valve failure is tearing. Cutting to form the free margins of the leaflets may introduce imperfections in the polymer which can lead to eventual failure of the valve. Therefore, cutting creates durability problems at the cut surfaces.

A factor in heart valve design is the consideration of energy loss. It is important to design a heart valve in a manner that will provide low energy loss. Energy loss considerations include forward pressure drop, leakage volume and closing volume. A major limitation of many known polymer valves is that, due to their geometry, they have significant planar coaption surfaces in the at rest or natural-state condition to provide good closure characteristics, but this causes the heart to work harder to open the valve. Other known polymer valves include geometries that are easier to open but the neutral position gap area is exaggerated. This increases closing volume which increases energy loss.

Finite element analysis of a flexible heart valve leaflet predict that the leaflet can buckle along the free margin during valve closing. This is because elements of the valve are compressed inwardly during valve closing. For example, the commissures are moved radially inwardly during valve closure. In addition, the free margins coapt, or engage during valve closure. As a result, the leaflets are exposed to compressive loading and become unstable. Buckling of the thin, flexible leaflets may occur and is most pronounced at the free margin. As the free margin buckles, a portion of the leaflet, between the mid-point and the commissure, bends away from a coaption plane formed by coapting free margins of an adjacent leaflet. Buckling is a complex structural failure and is difficult to analyze. If buckling at the free margin does occur, it can prevent complete coaption of the free margins. In addition, it can cause very high local stresses with each heart beat which can fatigue the valve.

Therefore, what is needed is a molded heart valve preferably of polymer or other suitable material, which includes thin, flexible leaflets that open easily under low opening pressure, that maintains stability under compressive loading that can occur on the free margin of the heart valve leaflet during closing, and which can maintain the free margin in tension during closing to avoid the problems associated with compressing the free margin as set forth above.

SUMMARY

One embodiment, accordingly, provides limitations related to free margin buckling and fatigue problems associated therewith. To this end, a heart valve includes a molded body having a plurality of leaflets. Each leaflet includes a scalloped free margin having opposite ends attached to a peripheral portion of the valve. Each free margin is adjacent each other free margin to form a gap therebetween. Each leaflet is of a first thickness, and at least a portion of each free margin is of a second thickness, greater than the first thickness.

A principal advantage of this embodiment is that the valve is more stable under compressive loading. By thickening only the free margin or a portion thereof, resistance to opening of the valve is not increased and buckling resistance is provided. In addition, providing the mid-portion of the leaflets below the commissures maintains the free margins in tension during valve closure which also provides resistance to buckling.

BRIEF DESCRIPTION OF THE DRAWING FIGURES

FIG. 6 is a frontal view illustrating an embodiment of a leaflet configuration.

FIG. 6A is a view taken along line 6A—6A of FIG. 6.

FIG. 6B is a view taken along line 6B—6B of FIG. 6.

FIG. 7 is a frontal view illustrating another embodiment of a leaflet configuration.

FIG. 7A is a view taken along line 7A—7A of FIG. 7.

FIG. 7B is a view taken along line 7B—7B of FIG. 7.

FIG. 8 is a frontal view illustrating a further embodiment of a leaflet configuration.

FIG. 8A is a view taken along line 8A—8A of FIG. 8.

FIG. 8B is a view taken along line 8B—8B of FIG. 8.

FIG. 9 is an isometric view illustrating a still further embodiment of a leaflet configuration.

FIG. 9A is a view taken along line 9A—9A of FIG. 9.

FIG. 9B is a view taken along line 9B—9B of FIG. 9.

DETAILED DESCRIPTION

Figure 1:
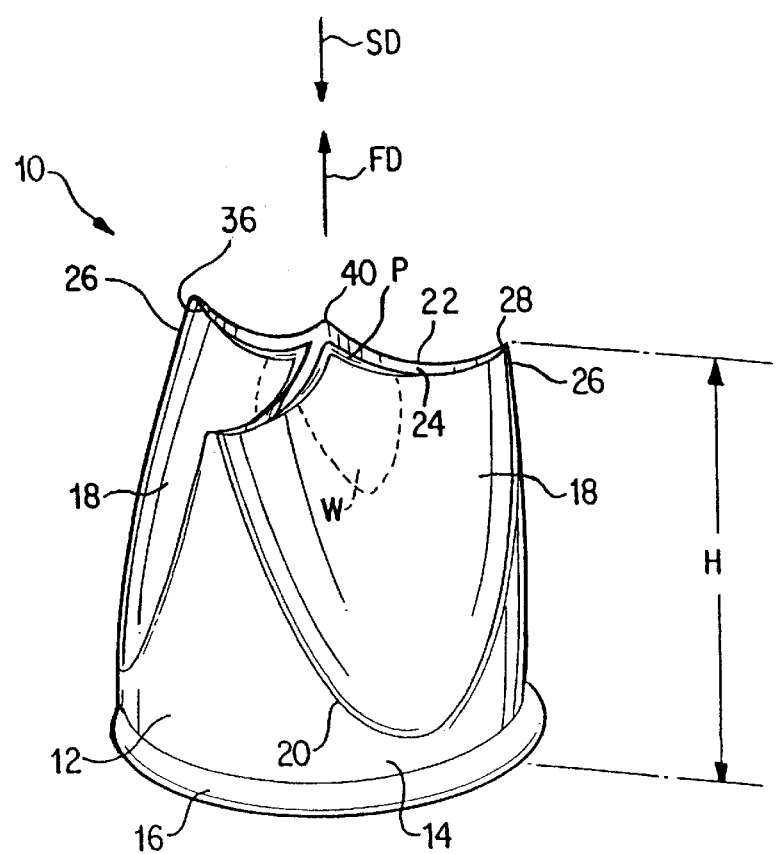
FIG. 1 is an isometric view illustrating an embodiment of a heart valve having leaflets in a natural state.
Figure 2:
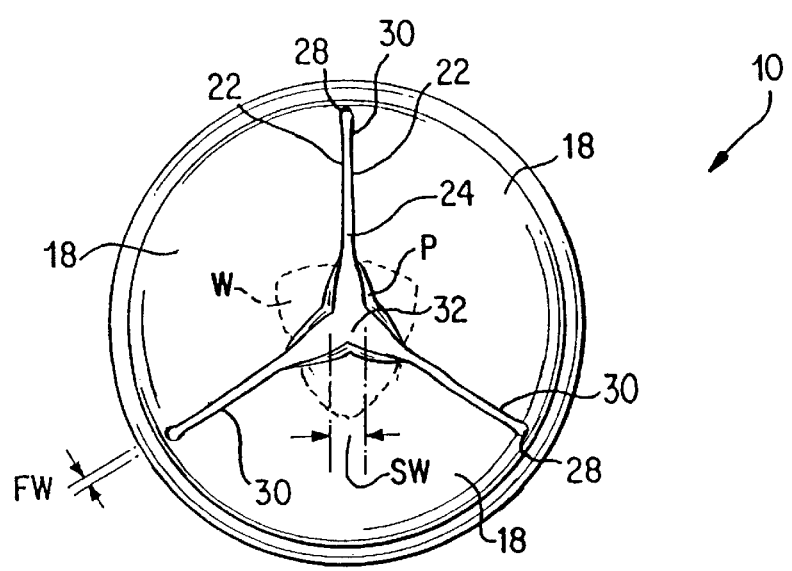
FIG. 2 is a top view illustrating an embodiment of the heart valve having leaflets in the natural state.

A heart valve is generally designated 10 in FIGS. 1 and 2. Heart valve 10 is formed as a one-piece molded biocompatible polymer body such as silicone or polyurethane and includes a generally annular peripheral body portion 12 which has a base 14. A sewing ring 16 may be formed with the base 14. Three flexible leaflets 18 are formed with body 12 and extend from an attachment curve 20 to terminate at a free margin 22 which is not in contact with another portion of body 12 when the valve is in a natural-state condition, i.e. the valve parts are at rest and are not under the influence of any pressure acting thereon. This is in contrast with the valve after installation when the pumping action of the heart sequentially and repeatedly opens and closes the valve by urging the leaflets in a first or opening direction indicated by the arrow designated FD, and then in a second or closing direction, opposite the first direction, indicated by the arrow designated SD.

The entire heart valve 10 is molded including a gap 24 which is preferably formed between each free margin 22. This is preferred over cutting to separate the valve leaflets after molding to form the free margins and improves the durability of the valve 10.

The attachment curve 20 defines a coupling between each leaflet 18 and the peripheral body portion 12, and also defines three shaped posts 26 which comprise an extension of body 12 terminating at a commissure 28 where gap 24 ends. This corresponds to the location where each leaflet 18 comes together with an adjacent leaflet. Posts 26 and each commissure 28 are at a height H above base 14.

Each free margin 22, FIG. 2, terminates adjacent each other free margin 22 to form the natural-state non-uniform gap 24. Gap 24 includes three legs 30 in the tri-leaflet configuration illustrated. Each leg 30 has a substantially uniform first width FW. Each leg 30 extends between its respective commissure 28 and a central opening 32 of gap 24 which interconnects each leg 30. Central opening 32 has a maximum second width SW which is greater than the first width FW.

Figure 4:
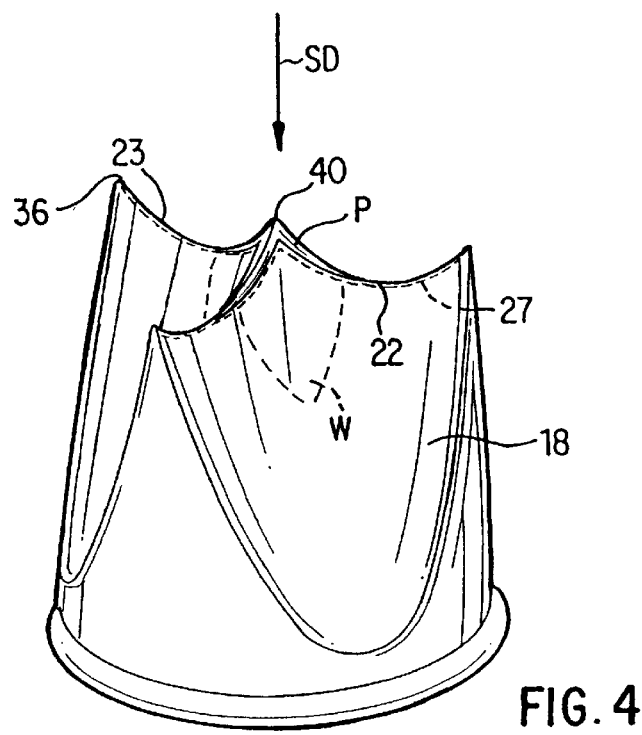
FIG. 4 is an isometric view illustrating an embodiment of the heart valve having leaflets in the closed position.

In order for gap 24 to be fully closed during operation of valve 10, FIGS. 1 and 2, each free margin 22 is scalloped to form a peak 36 at the opposite ends adjacent the respective commissures 28, and a mid-point peak 40 between the commissures 28 and adjacent the central opening 32. Each peak 36 and 40 is of the height H above base 14 which is substantially the same height H as posts 26 and commissures 28. Each mid-point peak 40, FIGS. 1, 2 and 4 is also of sufficient height to converge with each other mid-point peak 40 to a substantially closed position in response to reverse blood flow in the direction indicated by arrow SD, due to the pumping action of the heart. Scallops 23 formed in the free margin 22 between each peak 36 at the opposite ends, and the mid-point peak 40, allow for a reduced leaflet gap 24 adjacent the legs 30, and also increase the overall length of the free margin 22. The peaks 40 cooperate upon closure of valve 10 to allow for sufficient material at the central opening 32 for coaption as indicated by the dotted lines 27 adjacent the scallops 23. If desired, the geometry of scallops 23, peaks 36 and 40 can be altered to tailor the profile of gap 24.

Figure 3:
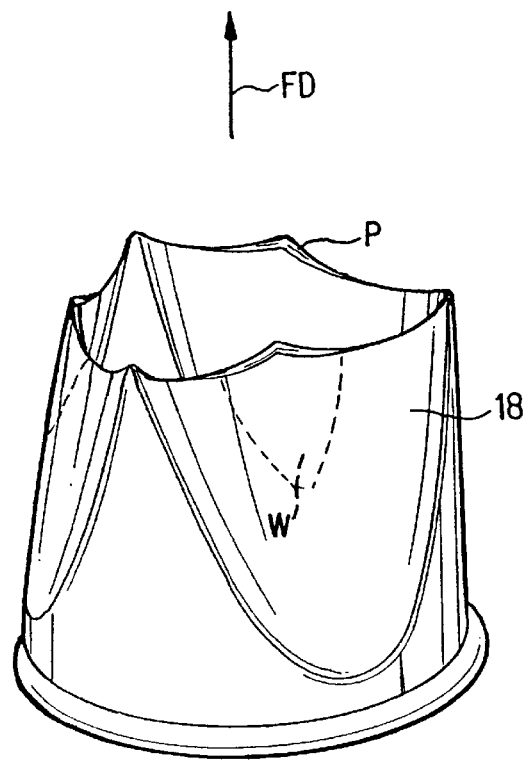
FIG. 3 is an isometric view illustrating an embodiment of the heart valve having leaflets in the open position.

In operation, when fluid flow is in the forward direction as indicated by arrow FD, FIG. 3, the pressure of the blood flow causes leaflets 18 to deflect to the open position. In this open position, the leaflets 18 define a large flow orifice such that the leaflets 18 present little resistance to fluid flow.

When fluid flow is in the reverse direction as indicated by arrow SD, FIG. 4, the pressure of the blood flow causes leaflets 18 to deflect to the closed position. In this closed position, the leaflets 18 occlude at the free margins 22 so that gap 24 is closed. Coaption occurs but is minimized due to the natural gap 24. Thus, closure to seal against reverse flow is accomplished as is improved occlusion and coaption.

Figure 5:
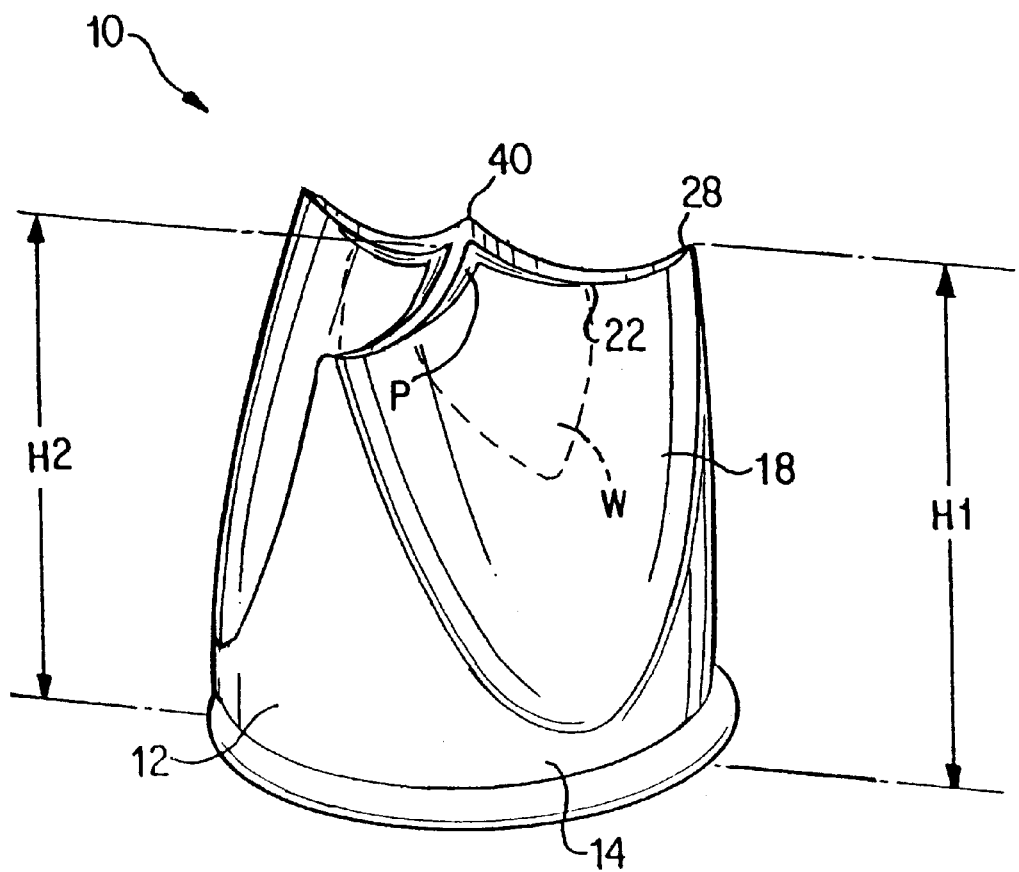
FIG. 5 is an isometric view illustrating another embodiment of the heart valve having leaflets in a natural state.

As illustrated in FIG. 5, the commissures 28 at opposite ends of each leaflet 18 are attached to the peripheral portion 12 of the valve 10 at a first height H1 above the base 14. The mid-point 40 of each free margin 22 is at a second height H2 above the base 4, which is less than the first height H1.

In each of the FIGS. 1–5, each leaflet 18 is of a first thickness generally throughout and includes a portion P which is of a second thickness greater than the first thickness. More specifically, FIGS. 6, 6A and 6B illustrate a leaflet 18 including a first portion 18a of a first thickness T1, and a second portion 18b of a second thickness T2. The second thickness T2 may extend as a bead B along the entire free margin 22. Alternatively, in FIGS. 7, 7A and 7B the second thickness T2 may extend as a wedge W only along a mid-portion 50 of the free margin 22. The remainder of leaflet 18 is of the first thickness T1 (see also FIGS. 1–5). Further, in FIGS. 8, 8A and 8B, the second thickness T2 may be formed as a combination of bead B extending along the entire free margin 22, including wedge W along mid-portion 50 of the free margin 22. It should be noted that in the embodiment of FIGS. 7, 7A and 7B, the free margin 22 is of the first thickness T1 adjacent a pair of opposite ends E of each leaflet 18. Still further, FIG. 9, 9A and 9B illustrate a leaflet 18 including a first portion 18a being of a first thickness T1, a second portion 18b, i.e. the free margin 22, including a second thickness T2, and a third portion 18c, i.e. only the mid-portion 50, being of a third thickness T3, greater than the second thickness T2.

As a result, one embodiment provides a heart valve including a molded body having a plurality of leaflets. Each leaflet includes a scalloped free margin having opposite ends attached to a peripheral portion of the valve. Each free margin is adjacent each other free margin to form a gap. Each leaflet construction is of a first thickness generally throughout. A portion of each free margin is of a second thickness greater than the first thickness. For example, the second thickness may extend along the entire length of the free margin between the opposite ends. Alternatively, the second thickness may extend only along a mid-portion of the free margin such that the free margin is of the first thickness adjacent the opposite ends. The opposite ends each terminate adjacent a commissure formed at the peripheral portion of the valve which defines an annular surface.

In another embodiment, a flexible leaflet heart valve includes a molded body having a base a peripheral portion and a plurality of leaflets. Each leaflet includes a free margin having opposite ends and a mid-portion between the opposite ends. The opposite ends are attached to the peripheral portion of the valve at a first height above the base. The mid-portion of each free margin is at a second height above the base, less than the first height. Each free margin is adjacent each other free margin to form a gap. Each leaflet is of a first thickness, and at least a portion of each free margin is of a second thickness which is greater than the first thickness. The free margin is scalloped and the second thickness may extend along the entire length of the free margin between the opposite ends. Alternatively, the second thickness may extend only along the mid-portion of the free margin such that the free margin is of the first thickness adjacent the opposite ends. The opposite ends each terminate adjacent a commissure formed at the peripheral portion of the valve which defines an annular surface.

In a further embodiment, a method of forming a flexible heart valve includes molding a one-piece body including a base, an annular peripheral portion including a plurality of commissures formed thereon, and a plurality of flexible relatively movable leaflets having a first thickness. Each leaflet is formed to include a scalloped free margin having opposite ends integrally connected to the peripheral portion adjacent the commissures and a mid-portion between the opposite ends. Each free margin is shaped to include a second thickness greater than the first thickness. Each free margin terminates adjacent each other free margin to define a natural-state, non-uniform gap therebetween which is maximized adjacent the mid-portion of each leaflet. The second thickness may extend along the entire length of the free margin between the opposite ends, or alternatively, may extend only along the mid-portion of the free margin such that the free margin is of the first thickness adjacent the opposite ends. The opposite ends connect to the peripheral surface at a first height above the base, and the mid-portion may be at a second height above the base, less than the first height.

As it can be seen, the principal advantages of these embodiments are that the valve is more stable under compressive loading. By thickening only the free margin or a portion thereof, resistance to opening of the valve is not increased and buckling resistance is provided. In addition, providing the mid-portion of the leaflets below the commissures maintains the free margins in tension during valve closure which also provides resistance to buckling.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A heart valve comprising:
    a molded body including a plurality of leaflets, each leaflet including a scalloped free margin having opposite ends, the opposite ends being attached to
    a peripheral portion of the valve;
    each free margin being adjacent each other free margin to form a gap therebetween; and
    each leaflet being a first thickness, and at least a portion of each free margin being of a second thickness, greater than the first thickness.

2. The heart valve as defined in claim 1 wherein the second thickness extends along the entire free margin between the opposite ends.

3. The heart valve as defined in claim 1 wherein each free margin includes a mid-portion between the opposite ends and the second thickness extends only along the mid-portion of the free margin.

4. The heart valve as defined in claim 1 wherein the peripheral portion of the valve is an annular surface including a plurality of commissures formed therewith.

5. The heart valve as defined in claim 4 wherein the opposite ends terminate adjacent a respective one of the commissures.

6. The heart valve as defined in claim 1 wherein the free margin is of the first thickness adjacent the opposite ends.

7. The heart valve as defined in claim 1 wherein each free margin includes a mid-portion between the opposite ends, the free margin being of the first thickness adjacent the opposite ends and being of the second thickness along the mid-portion of the free margin.

8. A flexible leaflet heart valve comprising:
    a molded body including a base, a peripheral portion and a plurality of leaflets, each leaflet including a free margin having opposite ends and a mid-portion therebetween, the opposite ends being attached to the peripheral portion of the valve at a first height above the base, the mid-portion of each free margin being at a second height above the base, less than the first height;
    each free margin being adjacent each other free margin to form a gap therebetween; and
    each leaflet being of a first thickness, and at least a portion of each free margin being of a second thickness, greater than the first thickness.

9. The heart valve as defined in claim 8 wherein the peripheral portion of the valve is an annular surface including a plurality of commissures formed therewith.

10. The heart valve as defined in claim 9 wherein the opposite ends terminate adjacent a respective one of the commissures.

11. The heart valve as defined in claim 8 wherein the free margin is scalloped and is of the first thickness adjacent the opposite ends.

12. The heart valve as defined in claim 8 wherein each free margin is scalloped, the free margin being of the first thickness adjacent the opposite ends and being of the second thickness along the mid-portion of the free margin.

13. The heart valve as defined in claim 8 wherein each free margin is scalloped and the second thickness extends along the entire free margin between the opposite ends.

14. The heart valve as defined in claim 8 wherein the second thickness extends only along the mid-portion of the free margin.

15. A method of forming a flexible heart valve comprising the steps of:
    molding a one-piece body including a base and a plurality of flexible relatively movable leaflets having a first thickness;
    forming each leaflet to include a scalloped free margin having opposite ends and a mid-portion between the opposite ends;
    shaping at least part of each free margin to include a second thickness greater than the first thickness;
    extending the opposite ends to integrally connect to a peripheral portion of the valve; and
    shaping each free margin to terminate adjacent each other free margin to define a continuous natural-state non-uniform gap therebetween which is maximized adjacent the mid-portion of each leaflet.

16. The method as defined in claim 15 wherein the step of extending the opposite ends includes the step of connecting the opposite ends to the valve at a first height above the base, and further comprises the step of shaping each free margin to position the mid-portion at a second height above the base, less than the first height.

17. The method as defined in claim 15 wherein the step of shaping at least a part of each free margin further comprises the step of extending the second thickness along the entire free margin between the opposite ends.

18. The method as defined in claim 16 wherein the step of shaping at least a part of each free margin further comprises the step of extending the second thickness along the entire free margin between the opposite ends.

19. The method as defined in claim 15 wherein the step of shaping at least a part of each free margin further comprises the step of extending the second thickness only along, the mid-portion of the free margin.

20. The method as defined in claim 16 wherein the step of shaping at least a part of each free margin further comprises the step of extending the second thickness only along the mid-portion of the free margin.

21. A heart valve comprising:
    a molded body including a plurality of leaflets, each leaflet having a scalloped free margin; and
    each leaflet being a first thickness, and only a portion of each free margin being of a second thickness greater than the first thickness.

22. The heart valve as defined in claim 21 further comprising a base and a peripheral portion including a plurality of commissures formed therewith, each free margin having opposite ends terminating at a respective one of the commissures, and a mid-portion therebetween, the opposite ends being attached to the commissures at a first height above the base, the mid-portion of each free margin being at a second height above the base, less than the first height.

23. A heart valve comprising:
    a molded body including a plurality of leaflets, each leaflet including, a free margin having opposite ends, the opposite ends being attached to a peripheral portion of the valve;
    each leaflet being of a first thickness;
    each free margin including a second thickness greater than the first thickness; and
    only a portion of each free margin being of a third thickness, greater than the second thickness.

* * * * *